United States Patent
Deng et al.

(10) Patent No.: US 7,409,861 B2
(45) Date of Patent: Aug. 12, 2008

(54) CONCENTRATION DETECTOR

(75) Inventors: Feng-Yi Deng, Taipei (TW); Ya-Chien Chung, Taipei (TW); Yu-Lin Tang, Taipei (TW); Yi-Hsien Chen, Taipei (TW)

(73) Assignee: Antig Technology Co., Ltd., Taipei (TW)

( * ) Notice: Subject to any disclaimer, the term of this patent is extended or adjusted under 35 U.S.C. 154(b) by 0 days.

(21) Appl. No.: 11/610,951

(22) Filed: Dec. 14, 2006

(65) Prior Publication Data

US 2007/0137299 A1    Jun. 21, 2007

(30) Foreign Application Priority Data

Dec. 16, 2005   (TW) .............................. 94221987 U

(51) Int. Cl.
   *G01N 9/00*   (2006.01)
(52) U.S. Cl. .......................................... 73/440; 73/454
(58) Field of Classification Search ................ 73/32 R, 73/61.41, 61.43, 61.44, 440, 451, 452, 454
   See application file for complete search history.

(56) References Cited

U.S. PATENT DOCUMENTS

| 1,701,404 A | * | 2/1929 | Dennis | ........................ 73/452 |
| 2,332,807 A | * | 10/1943 | Moore | .......................... 73/452 |
| 2,891,403 A | * | 6/1959 | Potter | ........................... 73/453 |
| 3,469,447 A | * | 9/1969 | Becker | ........................ 374/116 |
| 4,353,253 A | * | 10/1982 | Callahan | ....................... 73/454 |

* cited by examiner

*Primary Examiner*—Hezron E. Williams
*Assistant Examiner*—John Fitzgerald

(57) ABSTRACT

A concentration detector is adapted to detect the concentration of a liquid fuel in a container. The concentration detector comprises a rotating mechanism positioned underneath the level of the liquid fuel and having a rotational center. A first float having a specific gravity less than the specific gravity of the liquid fuel, a volume equivalent to "V" and a mass equivalent to "M". The distance between the mass center of the first float and the rotational center is "L". A second float connected with the first float and having a specific gravity less than the specific gravity of the liquid fuel, a volume equivalent to "V" and a mass equivalent to "r*M". The distance between the mass center of the second float and the rotational center is "L. The mass center of the second float, the rotational center and the mass center of the first float constitute an included angle of 120°. A third float connected to the first float and the second float and having a specific gravity less than the specific gravity of the liquid fuel, a volume equivalent to "V" and a mass equivalent to "$r^2$*M". The distance between the mass center of the third float and the rotational center is "L. The mass center of the third float, the rotational center and the mass center of the second float constitute an included angle of 120°. Thereby the variation in the concentration of the liquid fuel is acquired by inspecting the change in the rotational direction of the rotating mechanism.

10 Claims, 6 Drawing Sheets

| Concentration of methanol solution | Specific gravity of methanol solution |
|---|---|
| 3 % | 0.9937 |
| 4 % | 0.9917 |
| 5 % | 0.9896 |
| 6 % | 0.9875 |
| 7 % | 0.9854 |
| 8 % | 0.9833 |
| 9 % | 0.9812 |
| 10 % | 0.9791 |
| 11 % | 0.9771 |
| 12 % | 0.9750 |
| 13 % | 0.9729 |
| 14 % | 0.9708 |
| 15 % | 0.9687 |

FIG. 2

CONCENTRATION DETECTOR

FIELD OF THE INVENTION

The present invention relates to a concentration detector, and more particularly, to a concentration switch for detecting the concentration of liquid fuels in a fuel cell.

BACKGROUND OF THE INVENTION

A fuel cell is a power generator, which converts chemical energy stored within fuels and oxidants directly into electrical energy through reactions of its electrodes. The types of fuel cells are diverse and their classifications vary. According to the properties of their electrolytes, fuel cells can be divided into five types including alkaline fuel cells, phosphoric acid fuel cells, proton exchange membrane fuel cells, fused carbonate fuel cells, and solid oxide fuel cells. Wherein, a proton exchange membrane fuel cell includes a so-called direct methanol fuel cell (DMFC), which directly uses methanol as fuels without modifying the same into hydrogen gas. This is also at present a technique that can generate relatively high power. Such fuel cells may be applied to large power plants, vehicular power generators, portable power supplies, and so forth.

It is essential to control the concentration of liquid fuels while commercializing such types of fuel cells as DMFC. Theoretically, fuels with lower concentrations produce less electricity, and fuels with higher concentrations produce more electricity. Accordingly, to maintain the concentration at a predetermined level, a concentration detector is needed to monitor the concentration of liquid fuels in real-time. As such, the electrical output of fuel cells can be regulated, and electronic products using the cells will not be damaged due to unsteady power supplied by the fuel cells.

SUMMARY OF THE INVENTION

It is a primary object of the invention to provide a concentration detector for a fuel cell, which constantly monitors the concentration of liquid fuels required by a fuel cell, and responds in real-time if the concentration is changed.

In accordance with the aforementioned objects of the invention, a concentration detector is provided, which is adapted to detect the concentration of a liquid fuel in a container. The concentration detector comprises a rotating mechanism positioned underneath the level of the liquid fuel and having a rotational center. The rotating mechanism comprises a first float having a specific gravity less than the specific gravity of the liquid fuel, a volume equivalent to "V" and a mass equivalent to "M". The distance between the mass center of the first float and the rotational center is "L" on an X-Y plane. The rotating mechanism also comprises a second float connected with the first float and having a specific gravity less than the specific gravity of the liquid fuel, a volume equivalent to "V" and a mass equivalent to "r*M". The distance between the mass center of the second float and the rotational center is "L" on an X-Y plane. The mass center of the second float, the rotational center and the mass center of the first float constitute an included angle of 120°, wherein r is a constant greater than zero. The rotating mechanism further comprises a third float connected to the first float and the second float and having a specific gravity less than the specific gravity of the liquid fuel, a volume equivalent to "V" and a mass equivalent to "r$^2$*M". The distance between the mass center of the third float and the rotational center is "L" on an X-Y plane. The mass center of the third float, the rotational center and the mass center of the second float constitute an included angle of 120°. Thereby the variation in the concentration of the liquid fuel is acquired by inspecting the change in the rotational direction of the rotating mechanism.

BRIEF DESCRIPTION OF THE DRAWINGS

The foregoing aspects, as well as many of the attendant advantages and features of this invention will become more apparent by reference to the following detailed description, when taken in conjunction with the accompanying drawings, wherein:

FIG. 2 shows a comparison table listing the relationship between the concentration and the specific gravity of the methanol solution;

DETAILED DESCRIPTION OF THE INVENTION

Figure 1A:
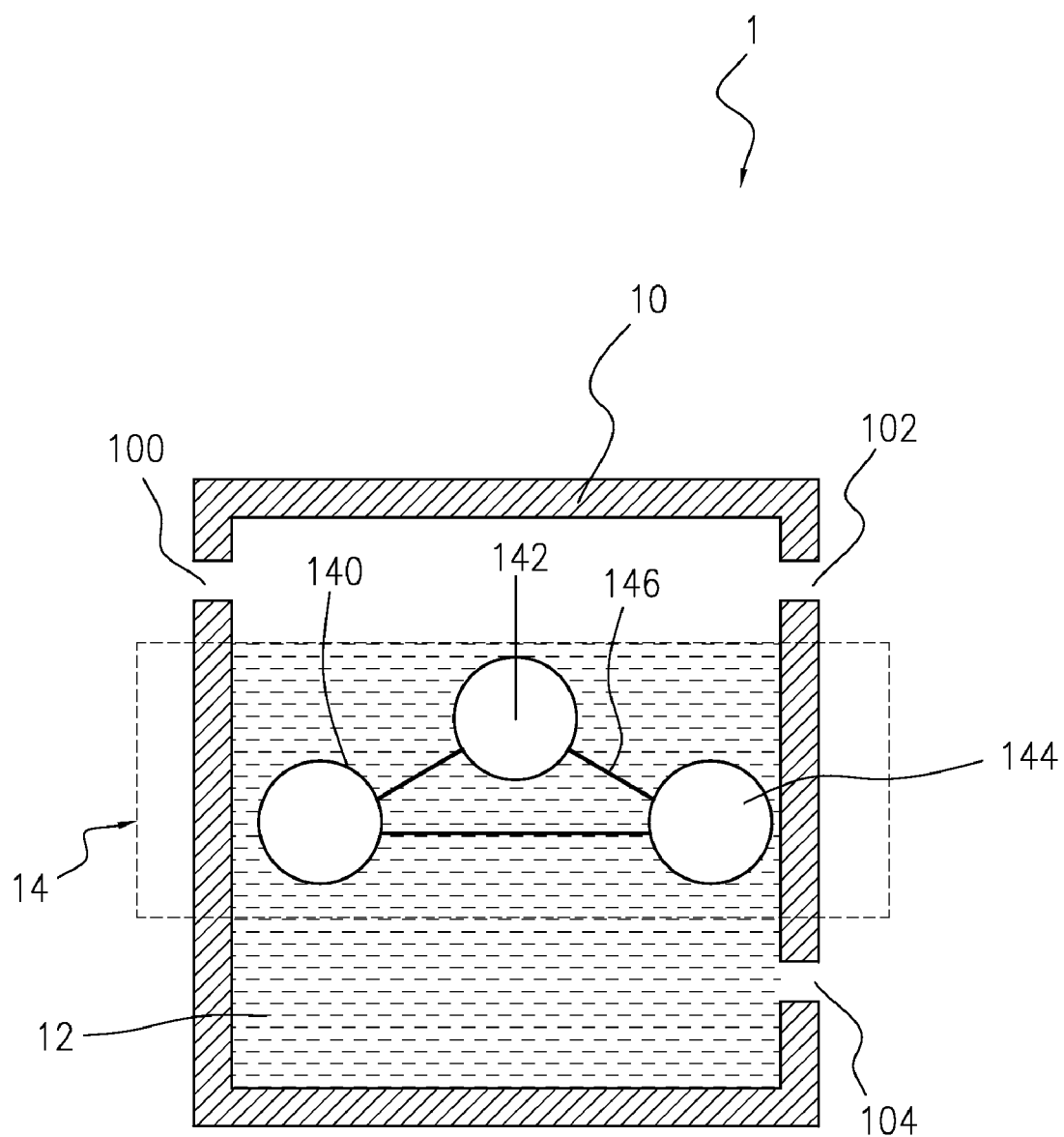
FIG. 1A is a side view of a concentration detector according to one embodiment of the invention.
Figure 1B:
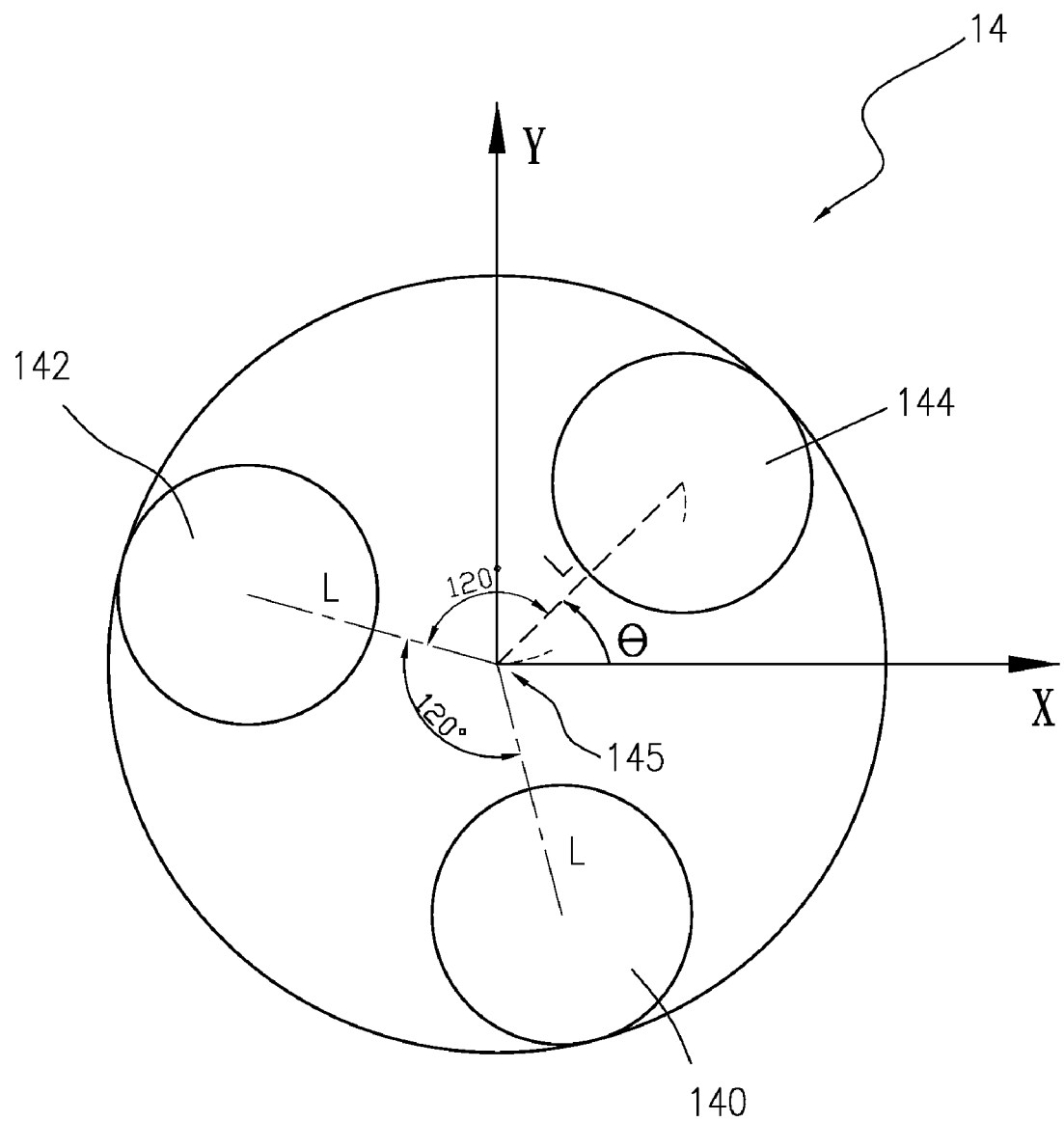
FIG. 1B is the top view of an exemplary status of the rotating mechanism in FIG. 1A.

FIG. 1A is a side view of a concentration detector according to one embodiment of the invention. FIG. 1B is the top view of an exemplary status of the rotating mechanism in FIG. 1A. In FIG. 1A, a fuel supply tank 1 includes a housing 10 with a hollow structure for the containment of fuels required by a fuel cell, i.e. liquid fuels 12. The liquid fuels 12 may be a methanol solution. The fuel supply tank 1 further includes a first inlet 100 adapted to inject fuels into the fuel supply tank 1, a second inlet 102 adapted for injecting an aqueous solution into the fuel supply tank 1 to dilute the concentration of fuels, and an outlet 104 used to drain fuels to an inlet on a flow plate (not shown) of a fuel cell.

In one embodiment, a concentration detector is utilized to sense the concentration of the liquid fuels 12 within the fuel supply tank 1. The concentration detector includes a rotating mechanism 14 positioned beneath the level of the liquid fuels 12, and a rotational center 145. The rotating mechanism 14 is rotated with an angle θ on the X-Y plane as illustrated in FIG. 1B. Referring to FIG. 1A, the rotating mechanism 14 includes a first float 140, a second float 142, and a third float 144, which are linked together by rods 146. The first float 140 has mass "M", the second float 142 has mass "r*M", and the third float 144 has mass "r$^2$*M", wherein r is a constant greater than zero. These floats may be balls made of anticorrosive materials, and have the same volume "V". In addition, the specific gravity of the floats is less than the specific gravity of the liquid fuels 12 ρ. With reference to FIG. 1B, the distances between the centers of mass of the floats and the rotational center 145 equals L on the X-Y plane. The center of mass of the second float 142, the rotational center 145 and the center of mass of the first float 140 constitute an included angle of 120° on the X-Y plane. The center of mass of the third float 144, the rotational center 145 and the center of mass of the second float 142 also constitute an included angle of 120° on the X-Y plane.

Figure 1C:
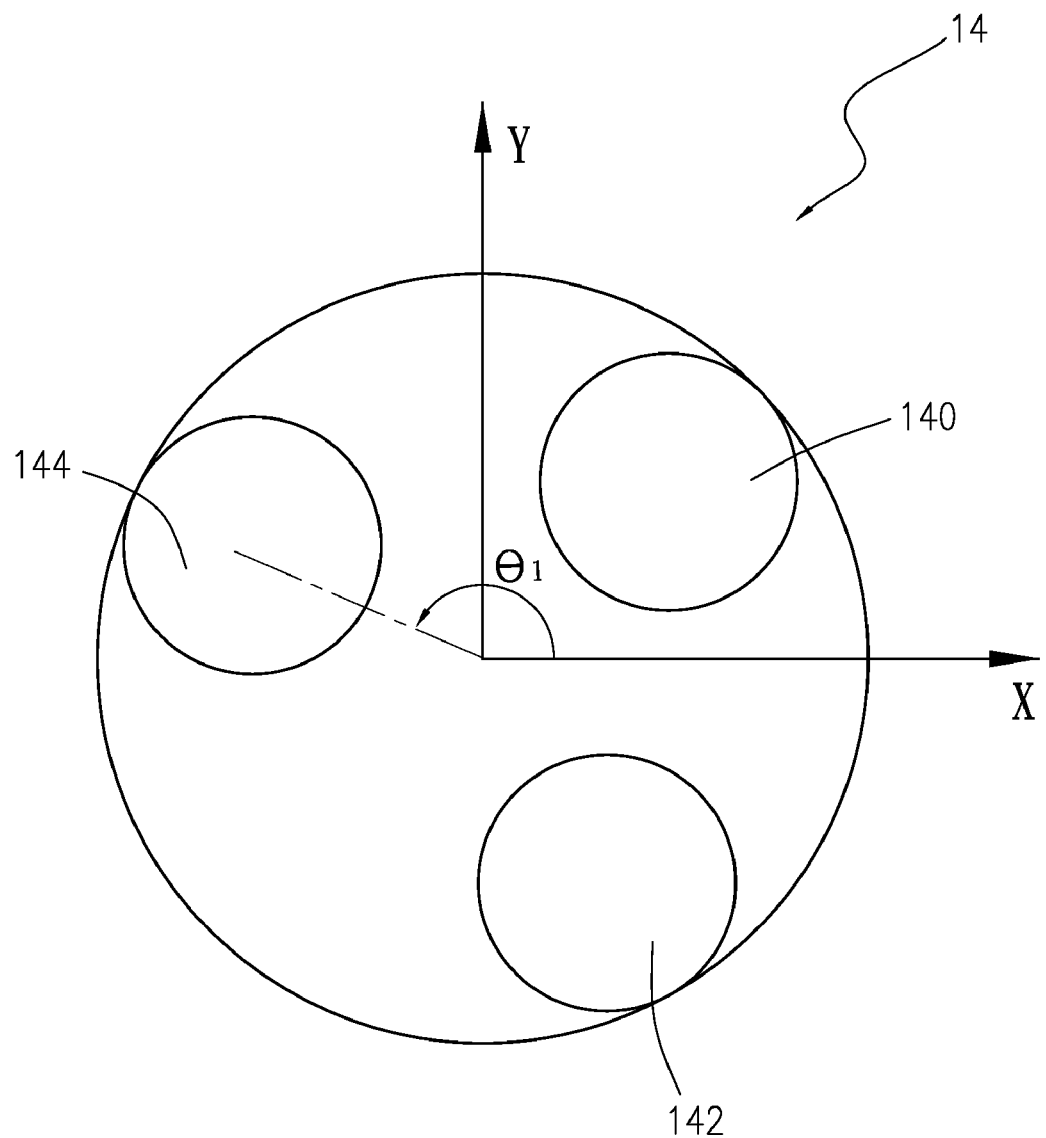
FIG. 1C is the top view of another status of the rotating mechanism in FIG. 1A.

FIG. 1C is the top view of another status of the rotating mechanism in FIG. 1A while the concentration of the liquid fuel 12 is changing. The buoyancy of each float 140, 142, 144 is different due to the variation of concentration, forcing the rotating mechanism 14 to turn at a rotational angle θ$_1$ on the X-Y plane. As a result, the first float 140, the second float 142 and the third float 144 are balanced according to the following torque equation:

$$(M-\rho*V)*L*\cos\theta+(r*M-\rho*V)*L*\cos(\theta+120°)+(r^2*M-\rho*V)*L*\cos(\theta+240°)=0,$$

where M, V, r, L are constants. Based on the torque equation $F(\theta, \rho)=0$, the rotating mechanism 14 is static under the level of the liquid fuels 12. Furthermore, the rotational angle $\theta_1$ of the rotating mechanism 14 has only one significant value; hence, the rotational angle $\theta_1$ is determined by the formula expressed below:

$$[\partial F(\theta,\rho)/\partial\theta]>0, \text{ where } \partial \text{ represents the partial differential.}$$

According to the embodiment, the rotational angle θ of the rotating mechanism 14 is detected when the concentration of the liquid fuels 12 is changed. Then, the specific gravity of the liquid fuels 12 ρ, is calculated from the torque equation, $F(\theta, \rho)=0$. Thereafter, the concentration of the liquid fuels 12 is computed. If the liquid fuels 12 are a methanol solution, the concentration of the methanol solution having specific gravity p can be converted via the comparison table in FIG. 2. Aside from the methanol solution, the concentration detector herein may be applied to other fuel cells employing liquid fuels with different specific gravities.

In one preferred embodiment, r is estimated by the following formula with a given specific gravity of liquid fuels, ρ:

$$[\partial F(\theta,\rho)/\partial\theta]=0, \text{ where } \partial \text{ represents the partial differential.}$$

Figure 3:
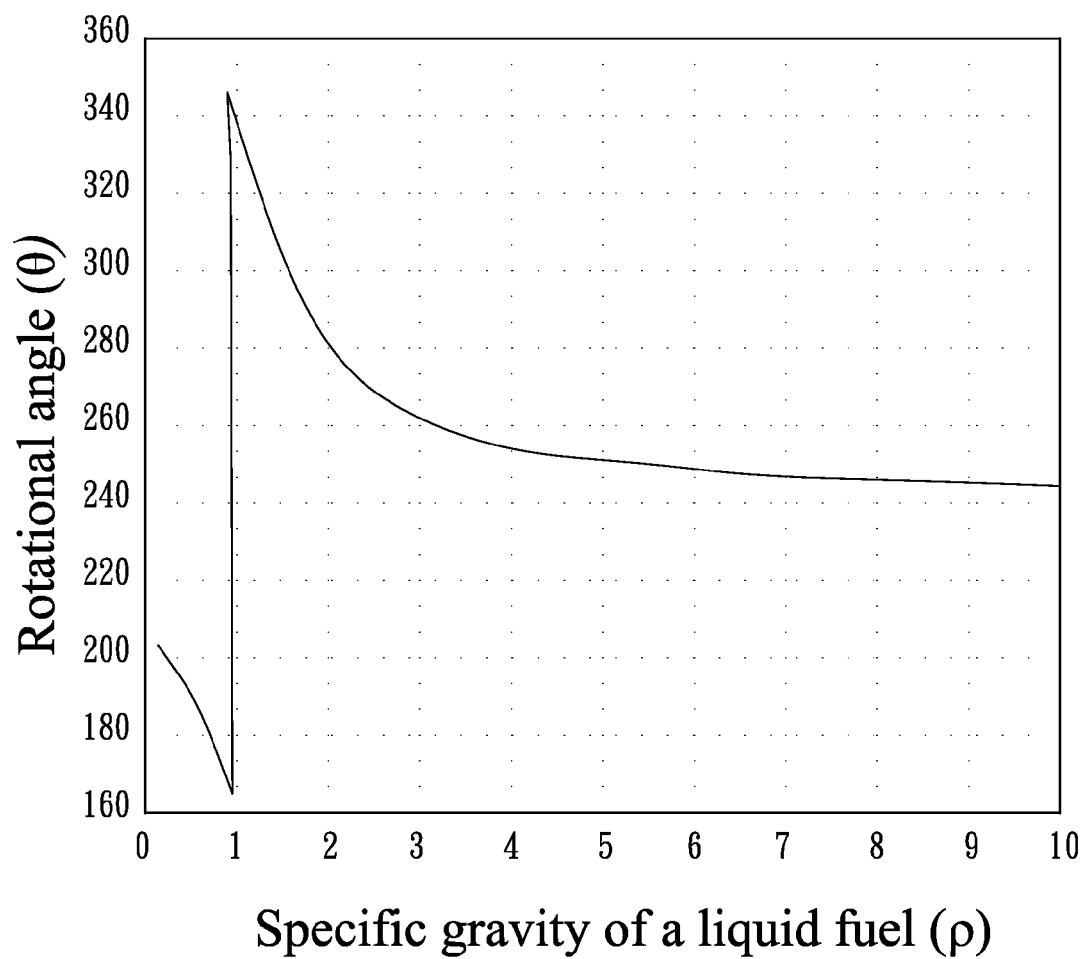
FIG. 3 is a plot showing the concentration of a liquid fuel vs. the rotational angle of a rotating mechanism in accordance with a concentration detector of a preferred embodiment of the invention.
Figure 4:
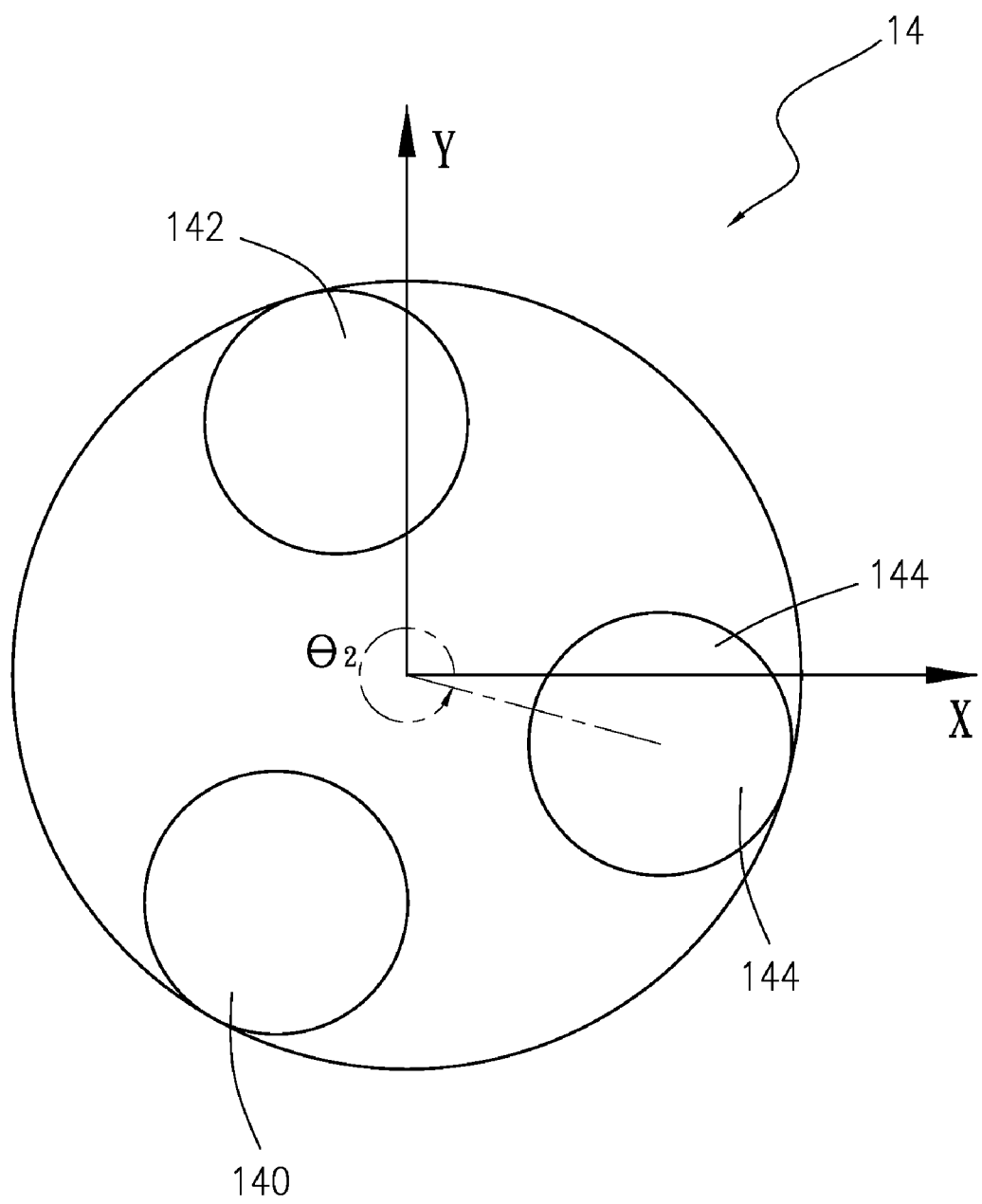
FIG. 4 is the top view of yet another status of the rotating mechanism in FIG. 1A.

FIG. 3 is a plot showing the specific gravity of liquid fuels ρ vs. the rotational angle of a rotating mechanism θ in accordance with a concentration detector of a preferred embodiment of the invention. Some basic data in the preferred embodiment are M=0.1 (g), r=2.83, L=13.8 (mm), and V=1 (cm3). Wherein, r is obtained by the formula, $[\partial F(\theta, \rho)/\partial\theta]=0$, as the specific gravity of liquid fuels ρ equals 0.96. It is apparent in FIG. 3 that a rotational angle θ corresponds to a specific gravity of a liquid fuel ρ. As shown, θ decreases as ρ increases from 0.1 to 1. That means the rotating mechanism 14 will rotate. As ρ approximates 0.96, the rotating mechanism 14 is operated as illustrated in FIG. 1C; meanwhile, $\theta_1=165°$. As ρ equals 0.96, the rotating mechanism 14 will rotate substantially at 180 degrees. Eventually, the rotating mechanism 14 is in the state of FIG. 4; meanwhile, $\theta_2=345°$. Because $\theta_1$ is very different from $\theta_2$, the change of the rotating mechanism 14 is easily observed by operators or means. Thus, the variation in the concentration of the liquid fuels 12 is acquired by inspecting the change in the rotational direction of the rotating mechanism 14. In FIG. 3, for example, the varied concentration is relevant to the concentration of the liquid fuels having the specific gravity ρ of 0.96.

To sum up, the invention possesses the following features and efficacies, wherein:
1. By using floats 140, 142, 144 that have mass in geometric series and identical volumes, and letting the floats and the rotational center 145 be equidistant may simplify the fabrication of the concentration detector. Consequently, the mass production of the concentration detector is easy and costs less; and
2. It is convenient to identify the concentration of the liquid fuels 12 since the concentration detector of the invention is sensitive. Moreover, the varying concentration of the liquid fuels 12 is monitored in real-time so that the concentration detector may serve as a concentration switch for sensing a particular concentration of liquid fuels.

While the invention has been particularly shown and described with reference to the preferred embodiments thereof, these are, of course, merely examples to help clarify the invention and are not intended to limit the invention. It will be understood by those skilled in the art that various changes, modifications, and alterations in form and details may be made therein without departing from the spirit and scope of the invention, as set forth in the following claims.

What is claimed is:

1. A concentration detector for detecting a concentration of a liquid fuel in a container, wherein the concentration detector comprises a rotating mechanism positioned underneath a level of the liquid fuel and having a rotational center, the rotating mechanism comprising:
   a first float having a specific gravity less than the specific gravity of the liquid fuel, a volume equivalent to "V" and a mass equivalent to "M", and for which the distance between the mass center of the first float and the rotational center is "L" on an X-Y plane;
   a second float connected with the first float, having a specific gravity less than the specific gravity of the liquid fuel, a volume equivalent to "V" and a mass equivalent to "r*M", wherein the distance between a mass center of the second float and the rotational center is "L" on the X-Y plane, and the mass center of the second float, the rotational center and the mass center of the first float constitute an included angle of 120°, where r is a constant greater than zero;
   a third float connected with the first float and the second float, having a specific gravity less than the specific gravity of the liquid fuel, a volume equivalent to "V" and a mass equivalent to "$r^2$*M", wherein a distance between the mass center of the third float and the rotational center is "L" on the X-Y plane, and the mass center of the third float, the rotational center and the mass center of the second float constitute an included angle of 120°,
thereby a variation in the concentration of the liquid fuel is acquired by inspecting a change in a rotational direction of the rotating mechanism.

2. The concentration detector of claim 1, wherein the rotating mechanism is rotatable at an angle θ on the X-Y plane, and the rotating mechanism is still under the level of the liquid fuel according to a torque equation $F(\theta, \rho)=(M-\rho*V)*L*\cos\theta+(r*M-\rho*V)*L*\cos(\theta+120°)+(r^2*M-\rho*V)*L*\cos(\theta+240°)=0$, where ρ represents the specific gravity of the liquid fuel.

3. The concentration detector of claim 2, wherein r is estimated by a given value of ρ input into a formula $[\partial F(\theta, \rho)/\partial\theta]=0$, where $\partial$ represents the partial differential.

4. The concentration detector of claim 1, wherein each float is a ball.

5. The concentration detector of claim 1, wherein the container is a fuel supply tank for supplying a fuel for a fuel cell.

6. The concentration detector of claim 1, wherein the liquid fuel is a methanol solution.

7. The concentration detector of claim 6, wherein each float is made of an anticorrosive material.

8. The concentration detector of claim 5, wherein the fuel supply tank further comprises a first inlet for injecting the fuel into the fuel supply tank.

9. The concentration detector of claim 8, wherein the fuel supply tank further comprises a second inlet for injecting an aqueous solution into the fuel supply tank.

10. The concentration detector of claim 9, wherein the fuel supply tank further comprises an outlet for draining the fuel to an inlet on a flow plate of the fuel cell.

* * * * *